United States Patent [19]
Cavanagh

[11] Patent Number: 5,421,898
[45] Date of Patent: Jun. 6, 1995

[54] METHOD AND ELEMENT FOR CONTROLLING RELEASE OF A DISINFECTANT FROM A SUBSTRATE

[75] Inventor: James W. Cavanagh, Ramsey, N.J.
[73] Assignee: Reckitt & Colman Inc., Wayne, N.J.
[21] Appl. No.: 838,977
[22] Filed: Feb. 21, 1992
[51] Int. Cl.⁶ ............................................... B08B 7/00
[52] U.S. Cl. .......................................... 134/7; 134/6; 134/22.19; 134/42; 427/389.9; 427/286; 427/288; 428/264; 428/289; 428/290
[58] Field of Search ........................ 427/286, 288, 389.9; 428/35.2, 35.5, 36.1, 264, 265, 290, 288; 252/91; 134/6, 7, 42

[56] References Cited

U.S. PATENT DOCUMENTS

| | | | |
|---|---|---|---|
| 2,292,921 | 8/1942 | Bock et al. | 428/264 |
| 3,324,500 | 6/1967 | Fuller et al. | 134/6 |
| 4,172,841 | 10/1979 | Danna et al. | 427/394 |
| 4,216,104 | 8/1980 | Gergely | 252/91 |
| 4,222,922 | 9/1980 | Rees | 427/154 |
| 4,272,393 | 6/1981 | Gergely | 252/91 |
| 4,289,815 | 9/1981 | Lee | 428/35 |
| 4,615,937 | 10/1986 | Bouchette | 428/288 |
| 4,772,492 | 9/1988 | Bouchette | 427/389.9 |
| 4,781,974 | 11/1988 | Bouchette | 428/288 |
| 4,837,079 | 6/1989 | Quantrille | 428/288 |
| 4,946,617 | 8/1990 | Sheridan et al. | 252/91 |
| 5,264,269 | 11/1993 | Kakiuchi et al. | 428/290 |

*Primary Examiner*—Anthony McFarlane
*Attorney, Agent, or Firm*—John R. Everett

[57] ABSTRACT

This present invention provides an element for controlling release of a quaternary disinfectant in aqueous solutions comprising a substrate coated with the residue of an aqueous composition of a water soluble polymer and a quaternary ammonium disinfectant characterized in that the water soluble polymer has weight average molecular weight of 85,000 to 186,000 and a degree of hydrolysis of 87 to 89 percent.

15 Claims, 3 Drawing Sheets

EFFECT OF CROSSLINK ON AIRVOL 540
HA4-1381 vs. HA4-1462
EXAMPLE 3

METHOD AND ELEMENT FOR CONTROLLING RELEASE OF A DISINFECTANT FROM A SUBSTRATE

FIELD OF THE INVENTION

The present invention relates to disinfectant elements and methods.

BACKGROUND OF THE INVENTION

Various fabric substrates bearing the residue of a dried disinfectant are known. As disclosed in U.S. Pat. 4,172,841, the usual method for preparing such substrates is to apply an aqueous solution of the disinfectant to the substrate. The solution is dried leaving a residue of the disinfectant on the substrate. When the substrate is used for disinfecting, for example a hard surface, it is wet with water and used to wipe the surface.

The problem is that disinfectant substrates prepared in this matter suffer a catastrophic release of the active disinfectant when the substrate is rinsed to remove accumulated soils. This catastrophic release renders the substrate ineffective for subsequent disinfecting uses such as cleaning hard surfaces. This limits the use of substrates to light duty uses that require no more than one or two uses of the substrate.

SUMMARY OF THE INVENTION

Figure 1:
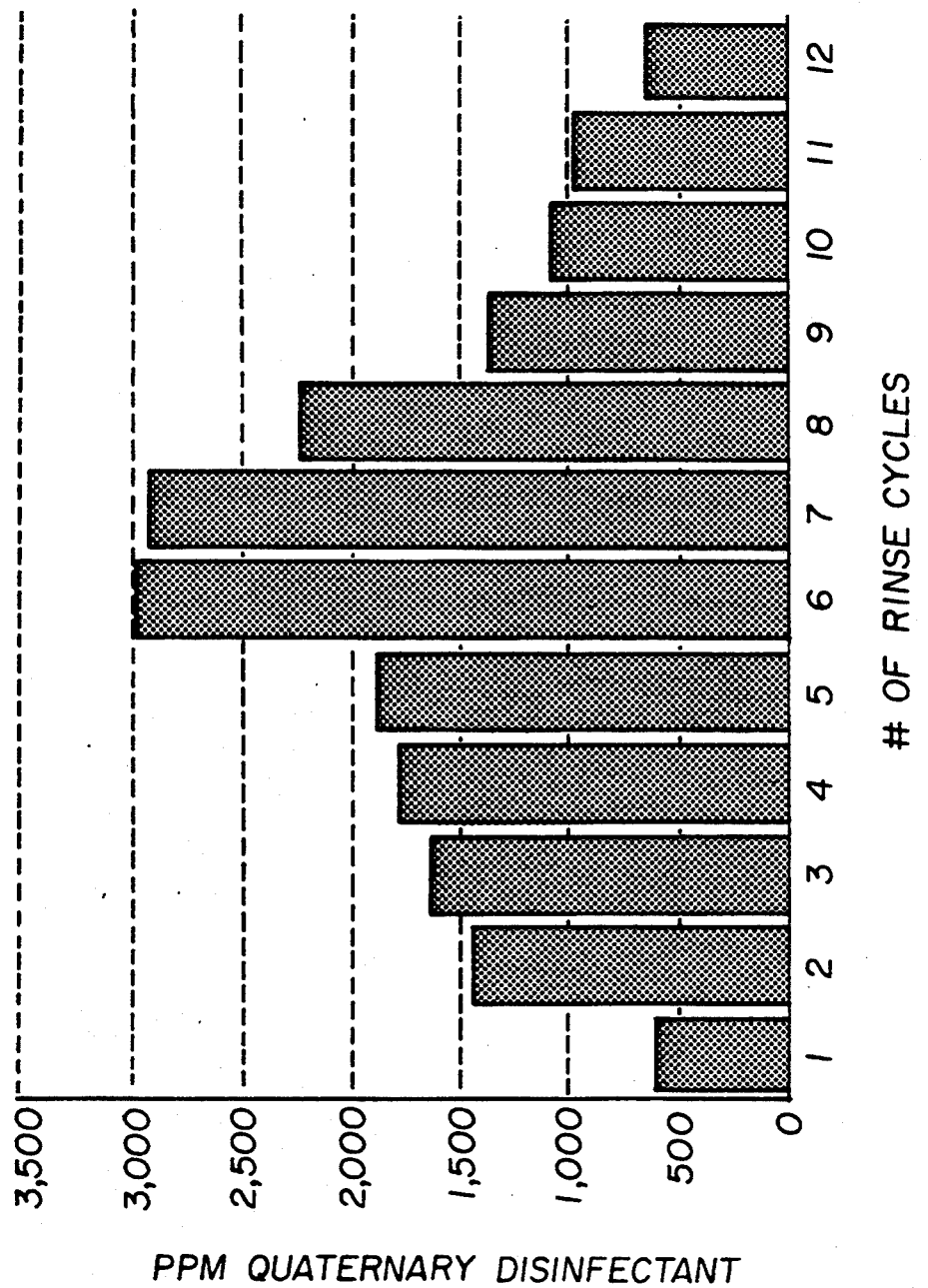
FIG. 1 shows the number of rinsings and the level of quaternary disinfectant remaining on a substrate of the invention after each rinse.

The present invention provides method of disinfecting surfaces comprising the steps of:
  (a) providing a substrate in which the release of disinfectants from the substrate is controlled by coating the substrate with a residue of an aqueous composition of a water soluble polymer and a quaternary disinfectant characterized in that the water soluble polymer has a weight average molecular weight of 85,000 to 186,000 (hereafter molecular weight), and a degree of hydrolysis of 87 to 89 percent, and
  (b) treating the surface with the substrate. Water soluble polymers having a molecular weight of 124,000 to 186,000 are particularly effective.

The degree of hydrolysis is important. For example molecules of polyvinyl alcohol (PVA) develop a greater affinity for each other due to hydrogen bonding as the degree of hydrolysis increases. In such polymers, having a degree of hydrolysis greater than 89 percent, the disinfectant component of the element is squeezed out of the substrate when the substrate is a film formed from the polymer.

The molecular weight range is also important. PVA having higher molecular weights are not available due to manufacturing limitations. PVA having lower molecular weights are to water soluble and will therefore release the quats at to great a rate.

The present invention also provides the element used in the above method.

The substrate meters the release of disinfectants over several rinsings in water, especially quaternary disinfectants (hereafter quats) thereby avoiding the catastrophic release of disinfectant that occurs with prior art disinfectant treated substrates. This invention permits water activated substrates to be an efficacious hard surface cleaning and disinfecting substrates through several thorough rinsings with water, thereby extending the useful life of the substrate.

DETAILS OF THE INVENTION

The method of the invention is straight forward. A hard surface cleaning substrate, such as a woven or nonwoven wipe, containing a residue of polymer and quat is wet with tap water to begin solubilizing, and therefore release, of the quat. The selected water-soluble polymer binds the quat to the wiping substrate over several rinsings.

Fabric substrates can include nonwoven or woven pouches, sponges, in the form of abrasive or non-abrasive cleaning pads. Such fabrics are known commercially in this field and are often referred to as wipes. Such substrates can be resin bonded, hydroentangled, thermally bonded, meltblown, needlepunched, or any combination of the former.

The nonwoven fabrics may be a combination of wood pulp fibers and textile length synthetic fibers formed by well known dry-form or wet-lay processes. Synthetic fibers such as rayon, nylon, orlon and polyester as well as blends thereof can be employed. The wood pulp fibers should comprise about 30 to about 60 percent by weight of the nonwoven fabric, preferably about 55 to about 60 percent by weight, the remainder being synthetic fibers. The wood pulp fibers provide for absorbency, abrasion and soil retention whereas the synthetic fibers provide for substrate strength and resiliency.

A useful nonwoven fabric is composed solely of wood fibers formed into a sheet by the well known air lay process and bound by a variety of resins known to those skilled in the art. A suitable fabric of this type is Style 835 from the Fort Howard Company.

Another suitable nonwoven material is modified Sontara® 8801, a spunlaced fabric containing a blend of 60% wood pulp fibers and 40% polyester fibers and having a unit weight of 1.85 oz./yd.$^2$ (approx. 62.7 g/m$^2$), prepared by producing a polyester fiber backbone by an air-lay process and laminating thereto a sheet of wood pulp fibers by water-needling thereby entangling the polyester and wood pulp fibers. This fabric substrate is available from E. I. DuPont de Nemours & Company. Another useful substrate used is an air layered nonwoven fabric substrate composed of wood pulp.

The substrate may also be a film forming material such as a water soluble polymer. Indeed, in a preferred embodiment of the invention the substrate is a self supporting film of the water soluble polymer used to retard release of the quat in aqueous solutions. Such self-supporting film substrates may be sandwiched between layers of fabric substrates and heat sealed to form a useful substrate. The free standing films can be extruded utilizing standard equipment to devolatilize the blend. Casting technology can be used to form and dry films or a liquid blend can be saturated into a carrier and then dried in a variety of known methods.

Other optional materials such as clays, fumed silica, calcium carbonate, or siliceous minerals can also be incorporated in or coated on substrates to provide abrasive properties, or improve film integrity. One or both sides of a substrate can be coated with abrasive materials to aid in cleaning. Additionally, one or both sides of a substrate can be coated with thermoplastic resins such as polyamide, polypropylene, polyethylene, polyester, ethylene acrylic acid, or starch based resins, such as Novon from warner-Lambert Company, to provide non-scratching abrasive properties.

The blend of water soluble polymer and quat coated on the substrates can also include nonionic surfactants, organic acid, colorant, and fragrance. The function of each such component are described below.

The water soluble polymer is selected to have an appropriate degree of hydrolysis and molecular weight to inhibit the catastrophic release of the quat in one or two washings. Polyvinyl alcohol (PVA), having the characteristics described under the summary of the invention, inhibits the release of disinfectant to a greater extent than molecules of lower molecular weight or a higher degree of hydrolysis. Other watersoluble polymers can be utilized such as polyvinylpyrrolidone and poly(ethylene oxide) having the solubility and degree of hydrolysis required by the invention defined herein.. In addition, plasticized grades of PVA, sold under the tradename "Vinex", can be substituted for the solution grades of PVA currently utilized and being sold under the AIRVOL tradename. AIRVOL 523 (MW 85,000-146,000) and 540 (MW 124,000-186,000) are examples of useful commercially available PVA. Also crosslinking PVA of lower molecular weights can be used. Crosslinking serves to increase the molecular weight and degree of hydrolysis of such polymers. Suitable crosslinking agents are well known in the art of PVA film compounding and are frequently described in the same promotional brochures describing PVA.

Nonionic surface active agents (surfactants) can be used as cleaning aids in blends of water soluble polymer and quat. Suitable nonionic surface active agents include those selected from:

(a) the polyethylene oxide condensates of alkyl phenols, having a straight or branched alkyl of from about 6 to about 12 carbon atoms, with ethylene oxide wherein the amount of ethylene oxide present is from about 3 to about 25 moles per mole of alkyl phenol;

(b) the condensation products of aliphatic alcohols with ethylene oxide of the formula $RO(C_2H_4O)_nH$ wherein R is straight or branched alkyl having from about 8 to about 22 carbon atoms and n is 3 to 40; and (c) polyoxyethylene polyoxypropylene block polymers.

Nonionic surfactants of type (a) above are marketed by GAF Corporation under the trademark Igepal®, e.g. Igepal® CA-420, an octylphenol condensed with an average of 3 moles of ethylene oxide, and by Rohm and Haas under the trademark Triton®, e.g. Triton® X-100, an octylphenol condensed with an average of 9 moles of ethylene oxide.

Nonionic surfactants of type (b) above are marked by Shell Chemical Company under the trademark Neodol®, e.g. Neodol® 23-6.5, the condensation product of $C_{12-13}$ linear primary alcohol with an average of 7 moles of ethylene oxide, and Neodol 91-8, the condensation product of $C_{9-11}$ linear primary alcohol with an average of 8 moles of ethylene oxide.

Nonionic surfactants of type (c) above are marketed by BASF Wyandotte Corporation under the trademark Pluronic® which conform to the formula $HO(CH_2CH_2O)_x(CH_3CH_3CHCH_2O)_y(CH_2CH_2O)_2HO, HO(CHCH_3CH_2O)_x(CH_2CH_2)_y(CHCH_3CH_2O)_2H$. Other examples of this type (c) are marketed under the trademark Tetronic from BASF, which are derived from the block copolymerization of ethylenediamine. Pluronic L92, used in the examples conforms to the formula $HO(CH_2O)_x(CH_3CHCH_2O)_y(CH_2CH_2)H$ where the average value of of x, y, and z are 10, 47, and 10 respectively. Pluronic L92 is oleophilic in nature and aids in the cleaning of hydrophobic soils. Plurafac C17 is also used in the following examples. Plurafac C17 is hydrophilic and helps in the removal of the more water soluble soil components. Other nonionic surfactants from the categories of betaines, and alkanolamides can be incorporated in the formulation.

The surface active agent is employed in an amount of from about 1 percent to about 70 percent of the water soluble composition and most preferably from about 10 percent to about 25 percent. In addition to the L92 and C17, a foaming agent Standamid SM (and alkanolamide) can be included. The purpose of the foaming agent is to provide a visual performance signal to the user and to aid cleaning. A quaternary ammonium disinfectant (quats) is a surface-active, water soluble disinfecting substance that has four carbon atoms linked to a nitrogen atom through covalent bonds, with the nitrogen or ammonium moiety of the salt forming a positively charged cation, rendering water solubility to the molecule, and with high molecular-weight aliphatic or-aromatic nonpolar side chains rendering a liophilic nature to the substance. Kills microorganisms on contact. Commercially available quaternary disinfectants (quats) include BTC 2125M and BTC 8358 are useful alkyl dimethyl benzyl ammonium chlorides. Other disinfecting agents include, but not limited to, orthophenylphenol, alkyl dimethyl ethylbenzyl ammonium chloride, biguanides, glutaraldehyde, or alkyl dimethyl ethylbenzyl ammonium chloride. The ratio of polymer to disinfectant is from 10:1 to 1:5, usually 5:1 to 1:3.

Colorants such as Xylene Blue VSG and Acid blue #9 may be incorporated into the blend of water soluble polymer and quat to provide a user with an endpoint indicator. That is when all of the quat has been exhausted from the substrate. The dye is released in a controlled fashion and can, for example substrate film strips until the quat is removed from the film strip.

Organic acids such as citric acid may be added to the blend to provide increased cleaning efficiency of mineral deposits and soap scum. Other weak organic acids, as well as appropriate chelating agents are also useful.

Materials such as clays, fumed silica, calcium carbonate, or silaceous minerals can also be incorporated in the substrate to achieve abrasive properties or improve film integrity.

EXAMPLES OF THE INVENTION

PVA is sifted into room temperature water under vigorous agitation. Heat is then applied between 150° F. to 180° F. while mixing to solubilize the PVA. when the PVA is dissolved nonionic surfactants, quats and crosslinking agent, if used are added. Each component is allowed to completely mix prior to the addition of the next component. The entire mixture is allowed to cool to room temperature. Then the remaining components are added such as the organic acid, colorant and fragrance. Using this procedure the blends in Table 1, examples 1-3, were prepared.

TABLE 1

| Component | Example 1 | Example 2 | Example 3 |
|---|---|---|---|
| Airvol 540 | 23.6 | 25.1 | 24.9 |
| Pluronic L92 | 8.1 | 8.5 | 8.4 |
| Plurafac C17 | 8.1 | 8.5 | 8.4 |
| Standamid SM | 6.5 | | |
| BTC 8358 | 37.5 | 40.3 | 40.1 |
| Citric Acid | 8.1 | 8.8 | 8.7 |
| Sunrez 700C (crosslinker) | — | — | 0.8 |
| Fragrance | 8.1 | 8.8 | 8.7 |

Each of the blends of examples 1-3 were cast as film substrates on glass and allowed to air dry at room temperature. The resulting dried films were cut into 7 inch by 0.5 inch strips. Obviously the width and thickness dimensions can be varied according to the solubility of the selected polymer. One or more of these strips are then sealed inside two 7 inch × 7 inch sheets of a nonwoven fabric. The edges of the fabric are sealed to each other along their respective edges to form a pouch within which the films are retained. An alternative substrate can be prepared using silk screen techniques to print the blend directly on a fabric substrate.

After drying each substrate, contained in the separate fabric pouches, was subjected to consecutive rinsings. A single rinse consisted of placing a substrate in 400 mL of deionized water in a container, closing the container and uniformly agitating. The substrate is then removed from the container and the excess liquid drained back into the container. This process is repeated a number of times. An aliquot of each sequential rinse step is then titrated to determine the amount of quat in the rinse aliquot using a standard analytical technique.

Example 1 results are shown in FIG. 1. The quat lasted through at least 12 rinsings with a peak of close to 3000 ppm in rinsings 6 and 7.

Figure 2:
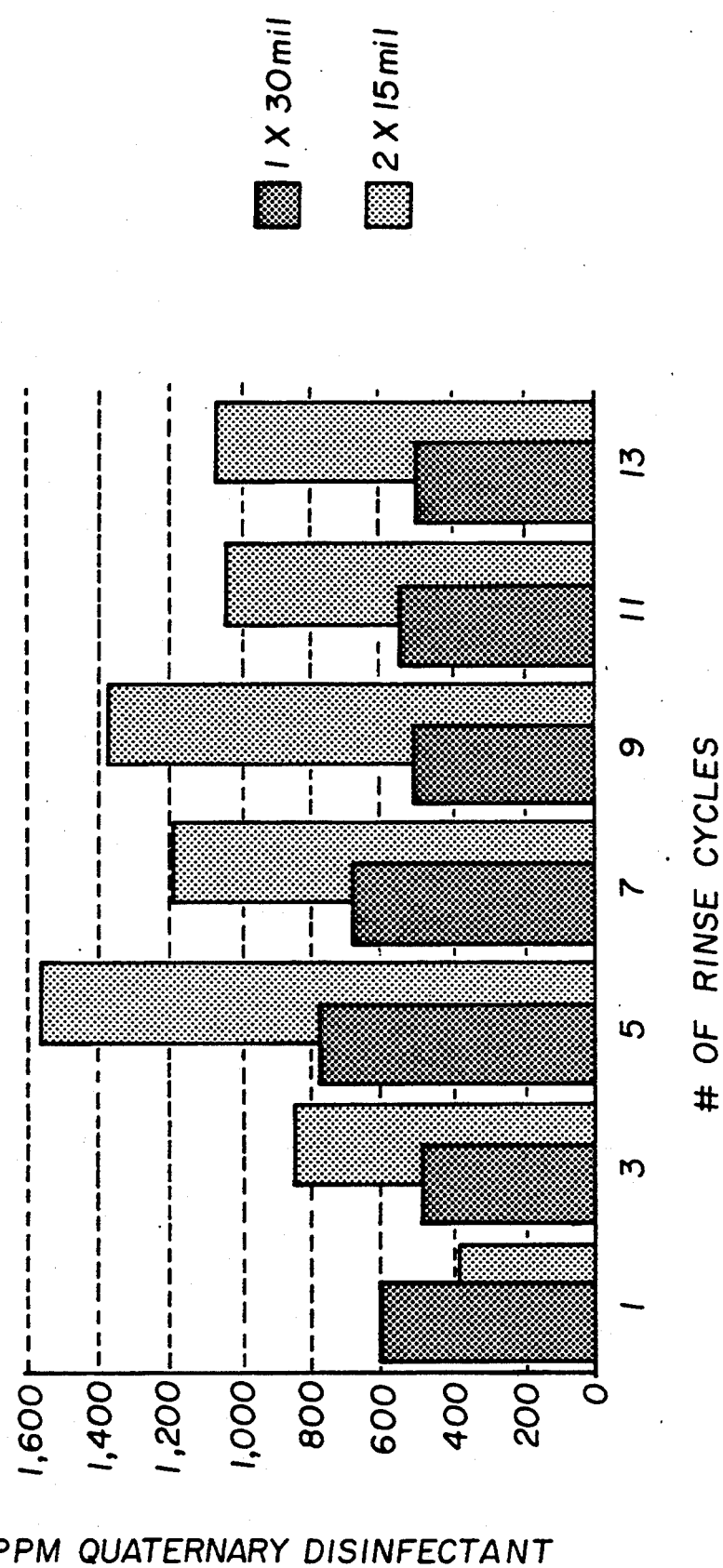
FIG. 2 shows the information as the thickness of the substrates of the invention are varied.

Example 2 results are shown in FIG. 2. Two film strips, each having the composition according to example 2, Table 1 were fused together to create a single strip having twice the thickness of a single film. Comparing fabric substrates containing roughly equal amounts of quats, the first having two strips of 15 mil film and the second having one 30 mil strip, it can be seen that the fabric substrate containing the single strip releases quats at a much slower rate. Therefore, a more soluble polymer can be used in a film of greater thickness to equal the release rate of a thinner film incorporating a less soluble polymer.

Figure 3:
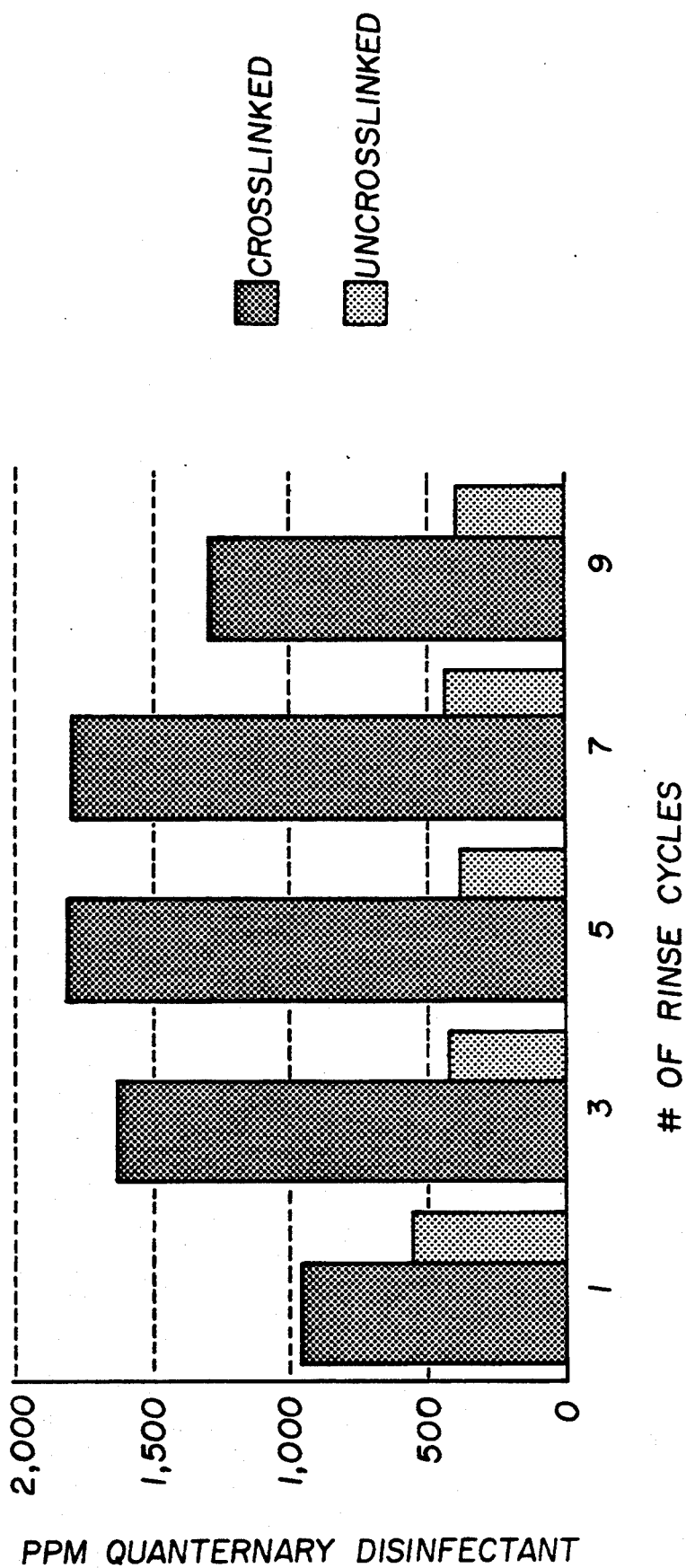
FIG. 3 provides the same information for substrates of the invention containing crosslinked Polyvinyl Alcohol.

Example 3 and FIG. 3 show the effect of using crosslinking agents to reduce the solubility of PVA compared to uncrosslinked PVA. This graph shows the effect of crosslinking by 2% by weight, based on the PVA, of Sunrez 700 which is a urea based crosslinking agent. Crosslinking a portion of the water soluble polymer can extend the useful life the fabric substrate or enable use of a more water soluble grades of PVA or other water soluble polymers.

The invention has been described in detail with particular reference to certain preferred embodiments thereof, but it will be understood that variations and modifications can be effected within the spirit and scope of the invention.

What is claimed is:

1. An element for controlling the release of a quaternary disinfectant in aqueous solutions comprising a substrate coated with the residue of an aqueous composition of both a) a water soluble polymer and b) a quaternary ammonium disinfectant characterized in that the water soluble polymer has weight average molecular weight of 85,000 to 186,000 and a degree of hydrolysis of 87 to 89 percent.

2. An element according to claim 1 wherein the water soluble polymer has a weight average molecular weight of 124,000 to 186,000 and a degree of hydrolysis of 87 to 89 percent.

3. The element of claim 1 wherein the substrate is selected from woven or non-woven fabrics.

4. The element of claim 1 wherein the substrate is a film-forming water soluble polymer.

5. An element according to claim 3 wherein the substrate is in the form of a pouch, sponge or an abrasive scouring pad.

6. An element according to claim 1 or 2 in which the substrate is a fabric dot coated with the residue of an aqueous composition of a water soluble polymer and said quaternary ammonium desinfectant characterized in that the water soluble polymer has weight average molecular weight of 124,000 to 186,000.

7. A fabric pouch containing said element according to claim 3 or 4.

8. An element according to claim 6 or 2 in which the residue is coated on the substrate in the form of one more stripes.

9. The element of claim 1 or 2 wherein the polymer is polyvinyl alcohol, polyvinylpyrrolidone or poly(ethylene oxide).

10. The element of claim 1 or 2 wherein the disinfectant is alkyl dimethylbenzyl ammonium chloride and the polymer is polyvinyl alcohol.

11. The element of claim 1 or 2 wherein the polymer is poly(ethylene oxide) or polyvinylpyrrolidone.

12. The element of claim 1 or 2 wherein the disinfectant is alkyl dimethylbenzyl ammonium chloride and the polymer is polyvinyl alcohol and the ratio of polymer to disinfectant is from 10:1 to 1:5.

13. A method of making an element from which the release of disinfectants is controlled when said element is wetted comprising the steps of:
(a) providing a substrate and
(b) coating the substrate with a residue of an aqueous composition of a water soluble polymer and a quaternary disinfectant characterized in that the water soluble polymer has weight average weight average molecular weight of 85,000 to 186,000 and a degree of hydrolysis of 87 to 89 percent.

14. The element of claim 1 or 2 wherein the disinfectant is selected from the group consisting of alkyl dimethyl benzyl ammonium chloride and alkyl dimethyl ethylbenzyl ammonium chloride.

15. A method of disinfecting surfaces, comprising the steps of:
(a) providing a substrate comprising a disinfectant;
(b) controlling release of the disinfectant from the substrate by coating the substrate with a residue of an aqueous composition of a water soluble polymer and a quaternary disinfectant wherein the water soluble polymer has weight average molecular weight of 85,000 to 186,000, and a degree of hydrolysis of 87 to 89 percent and
(c) disinfecting the surface by treating with the coated substrate.

* * * * *